United States Patent [19]

Jensen

[11] Patent Number: 5,076,784
[45] Date of Patent: Dec. 31, 1991

[54] ORTHODONTIC MIRROR

[76] Inventor: James L. Jensen, 18708 Dixie Hwy., Flossmoor, Ill. 60422

[21] Appl. No.: 569,925

[22] Filed: Aug. 20, 1990

[51] Int. Cl.$^5$ .............................................. A61B 1/24
[52] U.S. Cl. ..................................................... 433/30
[58] Field of Search .................................... 433/30, 31

[56] References Cited

U.S. PATENT DOCUMENTS

| 163,578 | 5/1875 | Cogswell | 433/30 |
| 1,021,639 | 3/1912 | Smith | 433/30 X |
| 3,158,935 | 12/1964 | Rosenthal | 433/30 |
| 3,300,859 | 1/1967 | Sanden | 433/30 |
| 3,539,247 | 11/1970 | Broussard | 433/30 X |

FOREIGN PATENT DOCUMENTS 0042865  2/1910  Austria ................................. 433/30

Primary Examiner—John J. Wilson
Assistant Examiner—Jeffrey A. Smith
Attorney, Agent, or Firm—Trexler, Bushnell, Giangiorgi & Blackstone, Ltd.

[57] ABSTRACT

An orthodontic mirror which is particularly useful for applying and aligning banding brackets to the teeth of the upper arch. The orthodontic mirror includes a handle having an elongated major axis and a mirror element attached to the handle at an obtuse angle. The mirror is generally rectangular and planar and extends in a plane at an obtuse angle with respect to the handle. The mirror element has a length which is substantially as great as a combined width of at least two teeth to which the brackets are to be applied and aligned and a width dimension of approximately one half of the length.

2 Claims, 1 Drawing Sheet

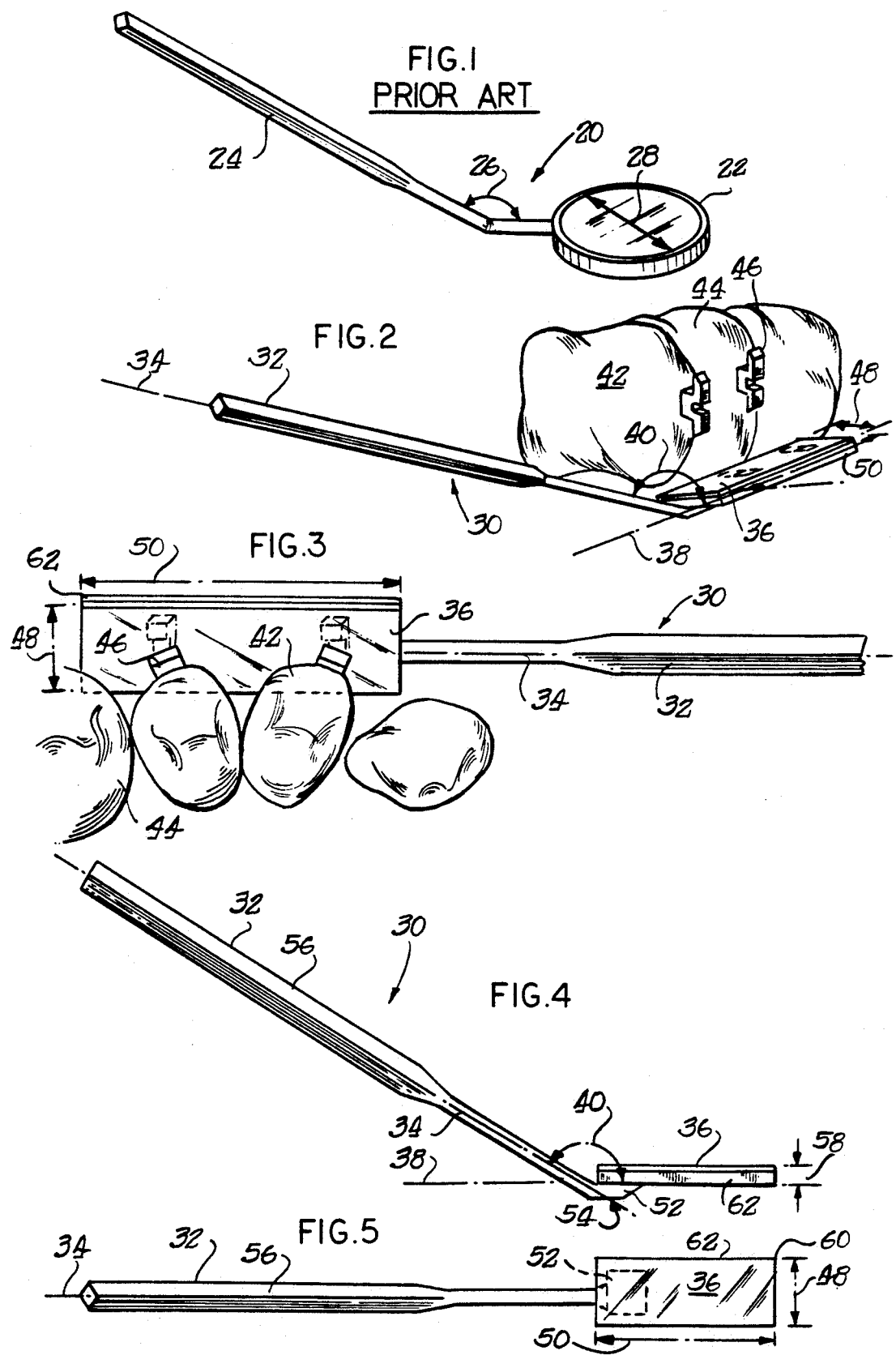

5,076,784

ORTHODONTIC MIRROR

BACKGROUND OF THE INVENTION

The present invention relates to a mirror which is particularly useful to orthodontists in attaching orthodontic devices to teeth.

It is now common practice to directly bond individual brackets to each tooth for subsequent attachment of wires or bands used for adjusting or maintaining the position of teeth. The brackets are discrete elements and are individually handled and secured to the teeth in a desired position. It is necessary that the bracket secured to one tooth be properly aligned with the brackets on adjacent teeth.

The brackets are bonded to the surfaces of the teeth. Placement and alignment of the brackets on the front teeth and in the lower arch is relatively easy since these teeth are readily visible. However, the teeth in the upper arch are sometimes difficult to see, and this is particularly true of the upper arch cuspids, bicuspids and molars. These teeth are positioned towards the rear of the arch and are located where the lip of the patient cannot be retracted sufficiently to expose the front face of the tooth for viewing. As a result, it is necessary to use a mirror inserted into the mouth so that the orthodontist can see the face of the tooth and the location where the bracket is to bonded.

Generally available prior art mirrors are circular with a diameter sufficient to see at least two teeth at once. As a result, however, these mirrors are so large that they cannot be positioned easily in an acceptable location in the mouth which may be packed with cotton and obstructed by mouth retractors and the like. If the diameter of the mirror is decreased to a size sufficiently small so that the mirror may be inserted into the mouth with ease, the mirror is so small that the orthodontist can see only one tooth at a time. This makes it difficult, if not impossible, to properly align the brackets on the adjacent teeth.

OBJECTS AND SUMMARY OF THE INVENTION

The object of the present invention is to provide an orthodontic mirror which improves the ease and efficiency of installation of orthodontic devices.

A more specific object of the present invention is to provide an orthodontic mirror which is generally rectangular and dimensioned for viewing at least two teeth simultaneously.

Briefly, and in accordance with the foregoing, the present invention comprises an orthodontic mirror for applying and aligning orthodontic devices to teeth. The present invention is particularly useful in applying banding brackets to cuspids, bicuspids and molars of the upper arch. The mirror includes an elongated handle having a major axis extending therethrough and a generally planar mirror element attached to the handle and positioned in a plane at an obtuse angle to the major axis. The mirror extends away from the handle and is generally rectangular in shape having a length dimension facilitating viewing of at least two teeth and a width dimension generally less than one half of the length dimension to facilitate ease of insertion into the mouth.

BRIEF DESCRIPTION OF THE DRAWINGS

The features of the present invention which are believed to be novel are set forth with particularity in the appended claims. The organization and manner of the operation of the invention, together with the further objects and advantages thereof, may be understood best by reference to the following description taken in connection with the accompanying drawings wherein like reference numerals identify like elements in which:

FIG. 1 is a perspective view of a prior art orthodontic mirror having a circular mirror element;

FIG. 2 is a perspective view of the orthodontic mirror of the present invention in its application environment viewing orthodontic devices applied to adjacent teeth;

FIG. 3 is a top view of the orthodontic mirror of the present invention positioned for viewing the orthodontic devices applied to adjacent teeth;

FIG. 4 is a side view of the present invention illustrating the elements and relative positions thereof; and FIG. 5 is a plan view of the orthodontic mirror as shown in FIG. 4.

DESCRIPTION OF THE ILLUSTRATED EMBODIMENT

While this invention may be susceptible to embodiment in different forms, there is shown in the drawings and will be described herein in detail, a specific embodiment with the understanding that the present disclosure is to be considered an exemplification of the principles of the present invention and is not intended to limit the invention to that as illustrated.

An example of a prior art mirror 20 is provided in FIG. 1. The prior art mirror has a generally circular mirror element 22 attached to a handle 24 at an angle 26 thereto. A diameter 28 of the generally circular mirror element 22 is dimensioned to accommodate viewing of at least two teeth. However, since the diameter 28 is consistent in all directions such a mirror element 22 is extremely inconvenient when attempting to view teeth. Further, the mirror element 22 of the prior art mirror 20 makes it difficult to view two teeth simultaneously because only a diameter 28 is generally the dimension of two teeth and therefore only a portion of the two teeth can be viewed.

FIG. 2 shows the orthodontic mirror 30 of the present invention. The orthodontic mirror 30 has a handle member 32 with a major or elongated axis 34 extending therethrough. With reference to FIG. 4, a generally rectangular planar mirror element 36 is located in a plane 38 extending away from the handle 32 at an obtuse angle 40 with respect to the elongated axis 34.

The mirror element 36 may be positioned in front of adjacent faces 42 of adjacent teeth 44 to apply and align orthodontic devices 46, such as banding brackets, to be mounted to the faces 42. The mirror element 36 has a width dimension 48 which easily fits between the tooth faces 42 and an opposing covering lip portion (not shown). A length dimension 50 of the mirror element 36 permits viewing of at least two tooth faces 42 (reflections of the banding brackets 46 are shown in the surface of the mirror element 36).

FIG. 3 provides a top view of the orthodontic mirror 30 as shown in FIG. 2. The mirror 30, as shown in FIG. 2 and FIG. 3 is angled slightly from the horizontal to provide a reflection in the surface thereof of the banding brackets 46 mounted to the tooth faces 42. As shown in FIG. 3, the length dimension 50 accommodates or overlaps at least two and possibly three teeth 44, depending upon the size of the teeth. The narrow width dimension 48 is relatively small compared to the available space between the tooth faces 42 and the opposing covering lip (not shown) thus facilitating ease of insertion into the mouth and greater accuracy in placement of the orthodontic devices 46.

The side view of the orthodontic mirror 30 as shown in FIG. 4, provides an understanding of the relationship between the mirror handle 32 and the mirror element 36. The mirror element 36 is formed in the plane 38 which intersects the elongated axis 34 at the obtuse angle 40. Preferably the obtuse angle 40 is approximately 120°. A mounting portion 52 is formed on an end 54 of the handle member 32 distal a grip portion 56. The combined height dimension 58 of the mirror element 36 and the mounting portion 52 is minimized to further facilitate insertion and positioning of the mirror 30 in the oral cavity.

FIG. 5 provides a plan view of the orthodontic mirror 30 shown in FIG. 4. While the mirror 30 in FIG. 4 has a handle member 32 at an obtuse angle to the plane of the mirror 38 the plan view shows that the length dimension 50 of the mirror element 36 is generally parallel to the elongated axis 34. Preferably, the present invention has a mirror element 36 which is approximately 33 mm in the length dimension 50 and 13 mm in the width dimension 48. These dimensions provide a mirror element 36 having a width 48 which is less than approximately ½ of the length dimension 50. Further, corners 60 of the mirror element 36 may be rounded to further increase the ease of insertion removal from the oral cavity. A metal or rigid trim 62 is attached to a perimeter of the mirror element 36 to provide strengthening and coverage of the external surface of the mirror element 36.

While a preferred embodiment of the present invention is shown and described, it is envisioned that those skilled in the art may devise modifications of the present invention without departing from the spirit and scope of the appended claims.

I claim:

1. An orthodontic mirror particularly useful for applying and aligning orthodontic devices to teeth, said orthodontic mirror comprising: a handle member having an elongated axis; a mirror element attached to said handle member and located in a plane extending at an obtuse angle with respect to said elongated axis, said mirror element extending away from said handle and having a length at least substantially as great as a combined width of a plurality of teeth to which orthodontic devices are to be applied, and said mirror element being substantially rectangular having a width less than approximately ½ of said length providing a substantially complete field of view of the teeth being viewed, said mirror element having a length dimension of approximately 30 mm and a width dimension of approximately 13 mm.

2. An orthodontic mirror according to claim 1, wherein said obtuse angle is approximately 120°.

* * * * *